United States Patent
Levesque et al.

(10) Patent No.: US 9,845,929 B2
(45) Date of Patent: Dec. 19, 2017

(54) SUN TRACKING LIGHT DISTRIBUTOR SYSTEM

(71) Applicants: INSTITUT NATIONAL D'OPTIQUE, Québec (CA); CENTRE DE RECHERCHE INDUSTRIELLE DU QUEBEC, Québec (CA)

(72) Inventors: Marc Levesque, Saint-Augustin-de-Desmaures (CA); Denis Hotte, L'Ancienne-Lorette (CA); Denis Lepine, Québec (CA)

(73) Assignees: INSTITUT NATIONAL D'OPTIQUE, Québec (CA); CENTRE DE RECHERCHE INDUSTRIELLE DU QUEBEC, Québec (CA)

( * ) Notice: Subject to any disclaimer, the term of this patent is extended or adjusted under 35 U.S.C. 154(b) by 734 days.

(21) Appl. No.: 13/778,521

(22) Filed: Feb. 27, 2013

(65) Prior Publication Data
US 2013/0219781 A1    Aug. 29, 2013

Related U.S. Application Data

(60) Provisional application No. 61/604,344, filed on Feb. 28, 2012.

(51) Int. Cl.
*F21S 11/00*     (2006.01)
*A01G 33/00*    (2006.01)
(Continued)

(52) U.S. Cl.
CPC .......... *F21S 11/005* (2013.01); *A01G 33/00* (2013.01); *C12M 21/02* (2013.01); *C12M 31/06* (2013.01);
(Continued)

(58) Field of Classification Search
CPC ...... F21S 11/005; C12M 31/08; C12M 31/06; C12M 21/02
(Continued)

(56) References Cited

U.S. PATENT DOCUMENTS

| 4,088,121 A | 5/1978 | Lapeyre |
| 4,153,039 A | 5/1979 | Carroll |

(Continued)

FOREIGN PATENT DOCUMENTS

| WO | 2004074423 | 9/2004 |
| WO | 2011099016 A2 | 8/2011 |

OTHER PUBLICATIONS

Zijffers et al., Design Process of an Area-Efficient Photobioreactor, Mar Biotechnol, Feb. 2008, pp. 404-415, Spinger.

*Primary Examiner* — Avinash Savani
*Assistant Examiner* — Deepak Deean
(74) *Attorney, Agent, or Firm* — Fasken Martineau DuMoulin LLP; Isabelle Chabot

(57) ABSTRACT

A sun-tracking light distributor system for use in an open-ended photo-bioreactor having an aqueous liquid for a photosynthetic culture, comprising: at least one light distributor each including a concentrator supporting section with a light entry surface adapted to receive sunlight rays, an elongated rod section with a light distribution surface adapted to redirect the received sunlight rays within the aqueous liquid, a light concentrating element provided at the light entry surface which concentrates within the elongated rod at least a portion of the sunlight rays received at the light entry surface; a displacement system operatively connected to the light distributors and adapted to change an orientation of the light entry surface of the light distributors to track a solar position.

14 Claims, 17 Drawing Sheets

(51) Int. Cl.
*C12M 1/00* (2006.01)
*F24J 2/06* (2006.01)
*F21V 8/00* (2006.01)

(52) U.S. Cl.
CPC ............ *C12M 31/08* (2013.01); *C12M 41/08* (2013.01); *F24J 2/067* (2013.01); *G02B 6/0006* (2013.01)

(58) Field of Classification Search
USPC .................................................. 126/600, 906
See application file for complete search history.

(56) References Cited

U.S. PATENT DOCUMENTS

| | | | | |
|---|---|---|---|---|
| 4,194,949 A | * | 3/1980 | Stark | B01D 3/00 126/634 |
| 4,210,121 A | * | 7/1980 | Stark | B01D 3/00 126/573 |
| 4,626,065 A | | 12/1986 | Mori | |
| 4,952,511 A | * | 8/1990 | Radmer | C12M 21/02 362/340 |
| 5,581,447 A | * | 12/1996 | Raasakka | F21S 11/00 126/698 |
| 5,981,271 A | | 11/1999 | Doucha et al. | |
| 6,037,535 A | * | 3/2000 | Yoshino | A01G 9/243 126/605 |
| 7,813,061 B2 | * | 10/2010 | Steneby | E04D 13/033 136/246 |
| 8,033,047 B2 | | 10/2011 | Rasmussen et al. | |
| 8,184,372 B1 | * | 5/2012 | Gu | H01L 31/058 359/597 |
| 8,650,798 B1 | | 2/2014 | Armstrong et al. | |
| 9,201,228 B1 | * | 12/2015 | Steinmeyer | G02B 19/0009 |
| 2006/0191566 A1 | * | 8/2006 | Schaafsma | F24J 2/067 136/246 |
| 2008/0268302 A1 | * | 10/2008 | McCall | C12M 21/02 429/513 |
| 2008/0311649 A1 | | 12/2008 | Cloud et al. | |
| 2009/0148931 A1 | * | 6/2009 | Wilkerson | C12M 21/02 435/286.1 |
| 2009/0291485 A1 | | 11/2009 | Shigematsu et al. | |
| 2009/0305389 A1 | | 12/2009 | Willson et al. | |
| 2010/0028991 A1 | * | 2/2010 | McCall | F24J 2/1047 435/292.1 |
| 2010/0170149 A1 | | 7/2010 | Keeler et al. | |
| 2010/0212655 A1 | * | 8/2010 | Henkel-Wallace | F24J 2/12 126/605 |
| 2010/0216203 A1 | | 8/2010 | Trent et al. | |
| 2010/0248333 A1 | | 9/2010 | Bartilson | |
| 2011/0117631 A1 | | 5/2011 | Woerlee et al. | |
| 2011/0117632 A1 | | 5/2011 | Woerlee et al. | |
| 2011/0153087 A1 | * | 6/2011 | Cohen | F03G 6/067 700/275 |
| 2011/0197317 A1 | | 8/2011 | Wong | |
| 2013/0029403 A1 | | 1/2013 | Hazlebeck et al. | |

* cited by examiner

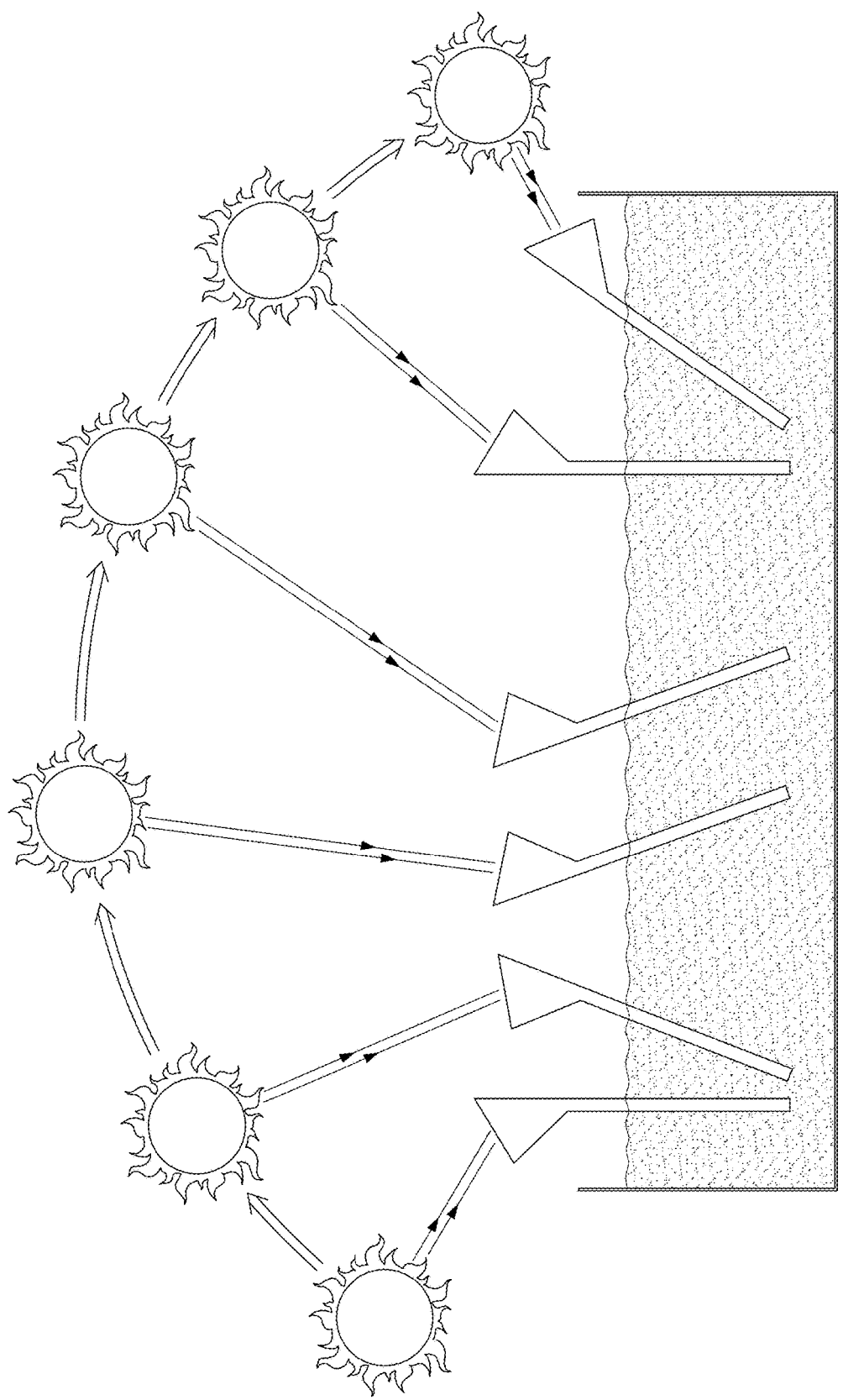

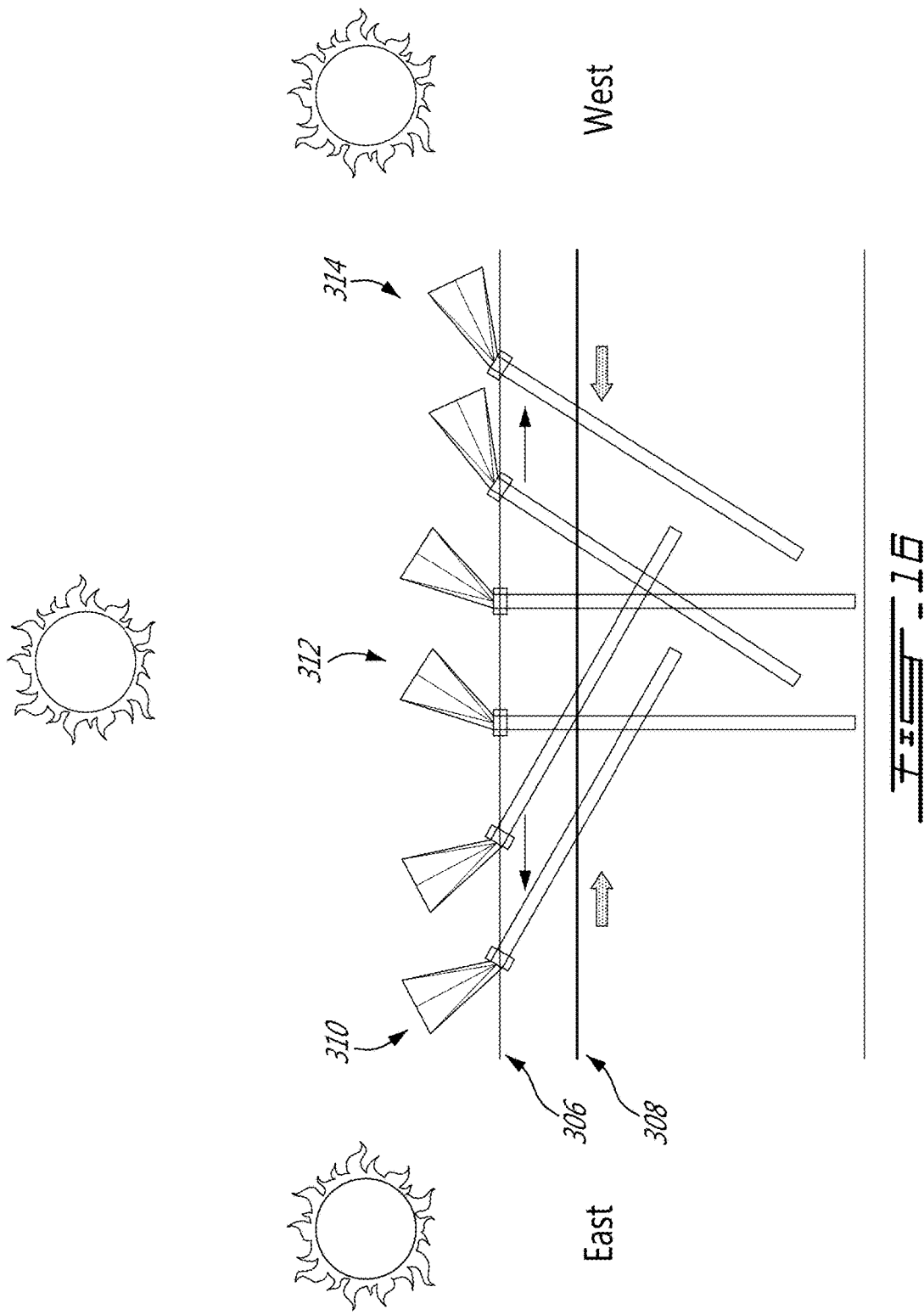

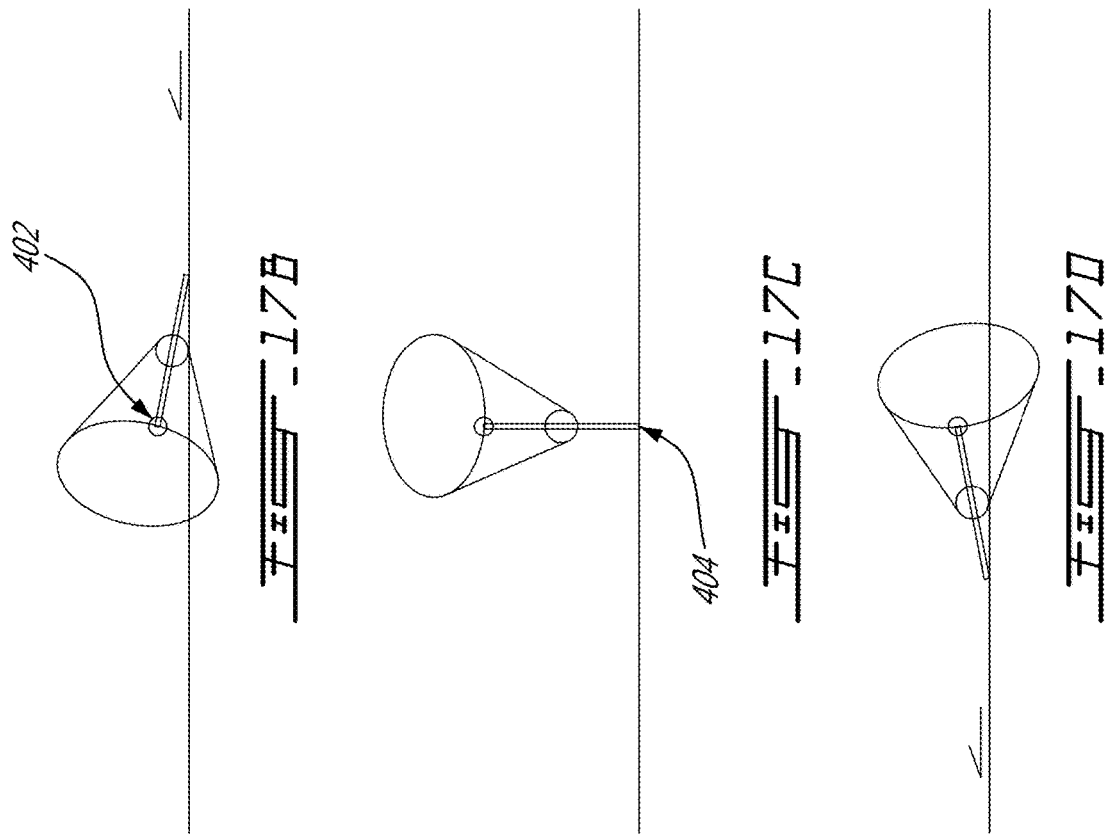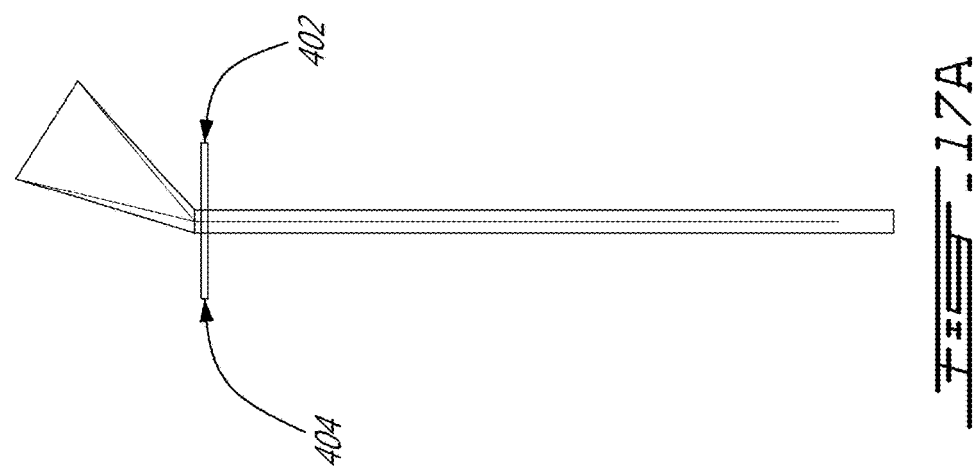

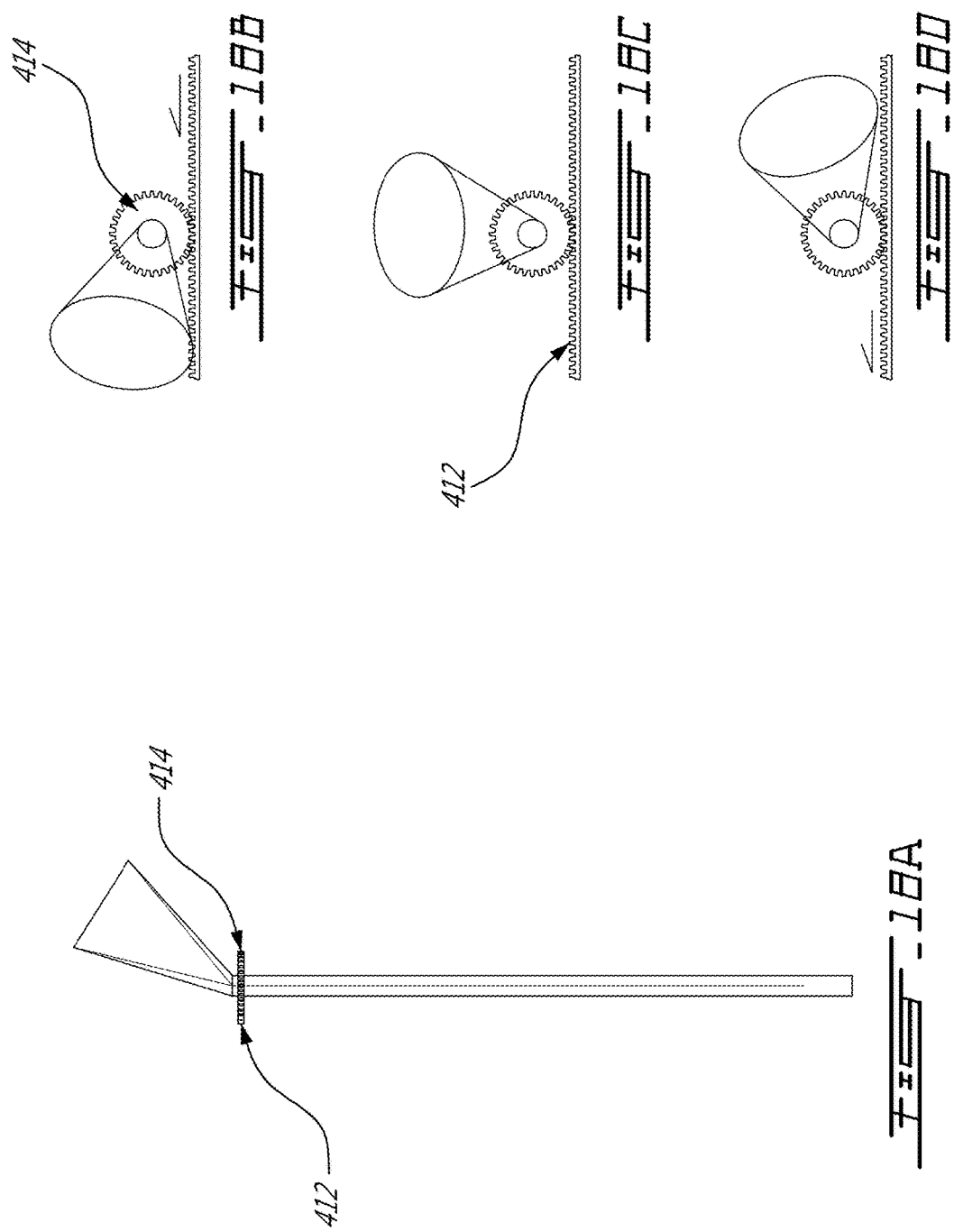

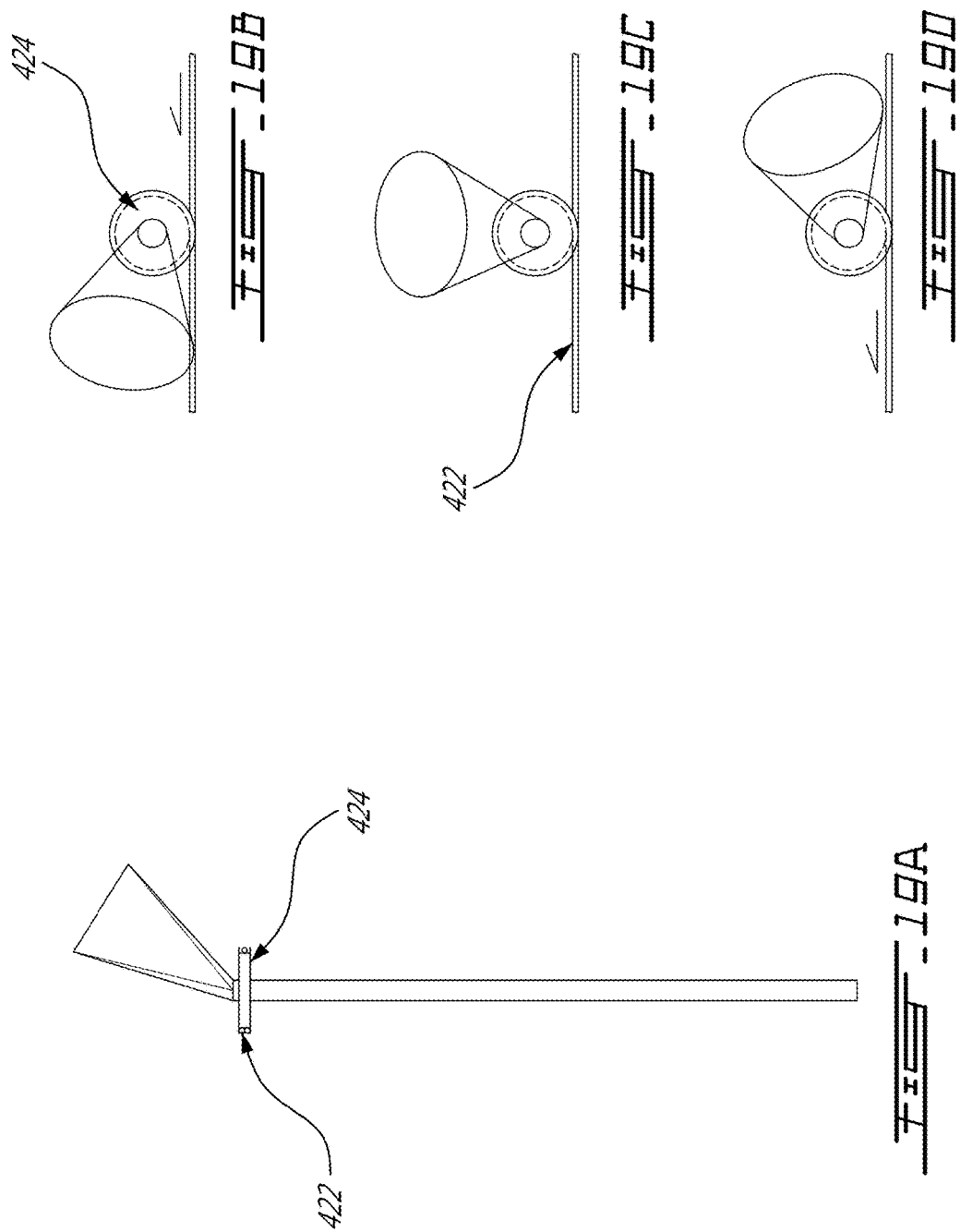

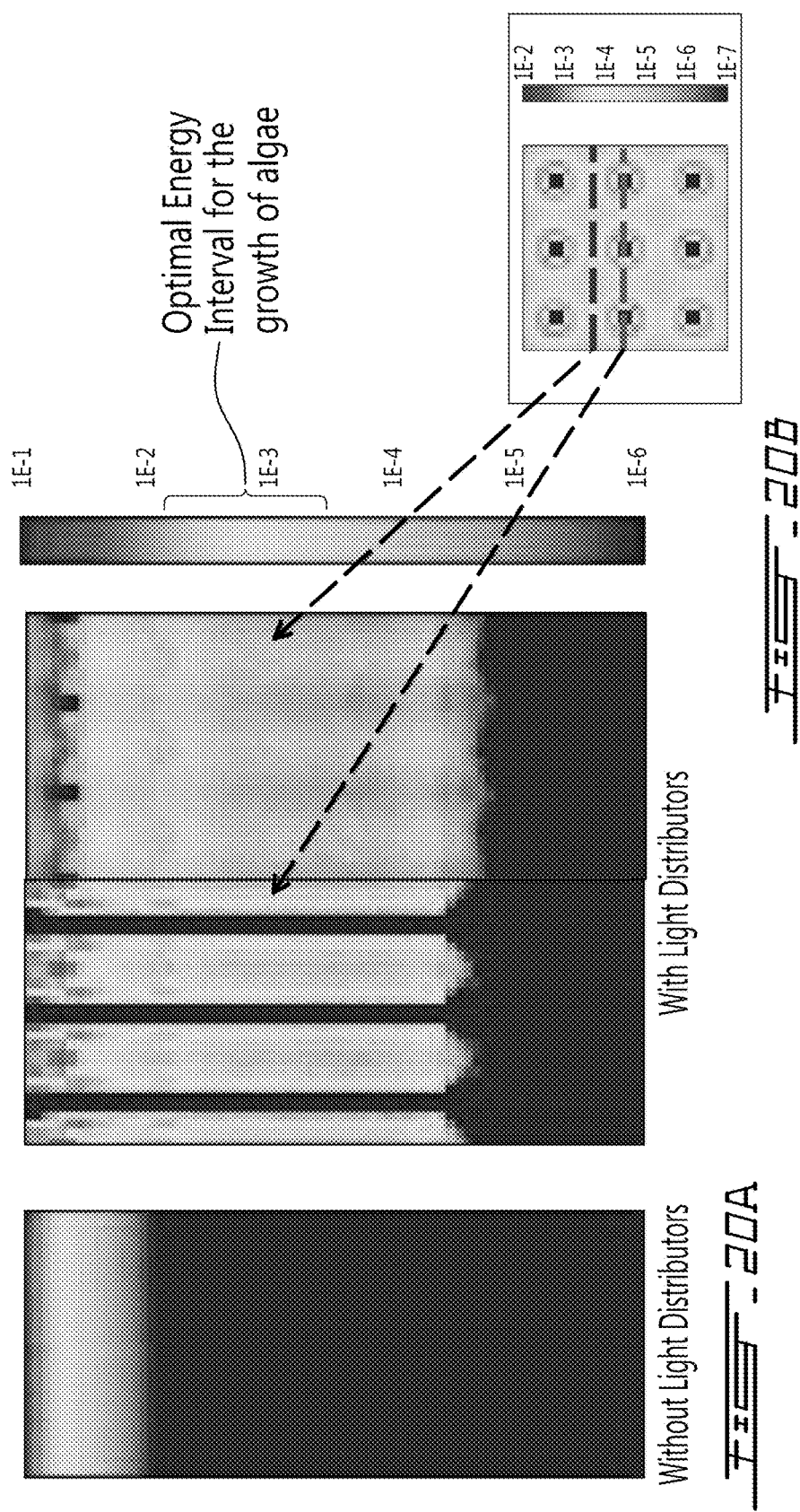

SUN TRACKING LIGHT DISTRIBUTOR SYSTEM

TECHNICAL FIELD

The invention relates to a light distributor system for use in open-ended photosynthetic culture aqueous systems which use the sun as a light source, for example for the production of algae. Light distributors are adapted to be oriented to track the sun by a displacement system and therefore provide a distribution of the light in the aqueous volume.

BACKGROUND OF THE ART

Photo-bioreactors for photosynthetic culture in aqueous liquids are known in the art. They are often used for the production of algae. Two main types are known in the art, the open-ended systems and the closed systems. The open-ended photo-bioreactor includes a reactor, basin or vessel. The vessel can be a naturally-occurring body of aqueous liquid, such as a portion of a pond, lake, brook, river, canal, sea, etc. It can be a man-made basin made of steel, plastic, concrete, etc. with a bottom wall and sidewalls. The aqueous liquid provided in the photo-bioreactor typically includes water and the photosynthetic culture organisms such as algae or micro-organisms. It can include other substances.

The prior art discusses different configurations to allow light to penetrate the aqueous liquid of the aqueous systems. These configurations either do not take into account the solar position throughout the day and throughout the year or can exhibit prohibitive optical losses or alignment precision requirements.

There is a need to improve light distribution in open-ended systems to benefit from exposure to as much light as possible from the sun.

SUMMARY

According to one broad aspect, there is provided a sun-tracking light distributor system for use in an open-ended photo-bioreactor having an aqueous liquid for a photosynthetic culture. The sun-tracking light distributor system comprises at least one light distributor each including a concentrator supporting section with a light entry surface adapted to receive sunlight rays, an elongated rod section with a light distribution surface adapted to redirect the received sunlight rays within the aqueous liquid, a light concentrating element provided at the light entry surface which concentrates within the elongated rod at least a portion of the sunlight rays received at the light entry surface; a displacement system operatively connected to the light distributors and adapted to change an orientation of the light entry surface of the light distributors to track a solar position.

According to another broad aspect, there is provided a sun-tracking light distributor system for use in an open-ended photo-bioreactor having an aqueous liquid for a photosynthetic culture. The sun-tracking light distributor system comprises at least one light distributor adapted to be at least partly immersed in the aqueous liquid in use, each light distributor comprising a body made of a transparent material allowing sunlight rays to pass therethrough, each light distributor including a concentrator supporting section with a light entry surface adapted to receive sunlight rays, the light entry surface being at an enlarged end of the concentrator supporting section, the light entry surface being provided above a surface of the aqueous liquid; an elongated rod section with a light distribution surface adapted to redirect the received sunlight rays within the aqueous liquid, the light distribution surface being along a sidewall of the elongated rod section, the light distribution surface being adapted to be at least partly immersed in the aqueous liquid in use, the elongated rod section being in optical communication with the concentrator supporting section to allow the received sunlight rays to travel within the body from the light entry surface to the light distribution surface; a light concentrating element provided at the light entry surface which concentrates within the elongated rod at least a portion of the sunlight rays received at the light entry surface; a displacement system operatively connected to the light distributor and adapted to change an orientation of the light entry surface of the light distributor to track a solar position with respect to at least one axis.

According to another broad aspect, a method for distributing light in an open-ended photo-bioreactor for a photosynthetic culture is provided. The method includes providing a sun-tracking light distributor system in the open-ended photo-bioreactor having an aqueous liquid; and changing an orientation of the light entry surface of the light distributor using the displacement system to allow tracking of the sun.

In the present specification, the term "transparent" is intended to mean a material which allows sunlight of the wavelength band of interest to pass therethrough with limited absorption in the material itself. For the production of algae, an example wavelength band of interest can be visible light in the range of 400 nm-700 nm.

BRIEF DESCRIPTION OF THE DRAWINGS

Having thus generally described the nature of the invention, reference will now be made to the accompanying drawings, showing by way of illustration example embodiments thereof.

FIG. 8A shows an example light distributor with the sun rays being distributed within the rod and FIG. 8B shows light distributors provided in an open-ended photo-bioreactor with a volume of aqueous liquid;

FIG. 11 includes FIG. 11A and FIG. 11B and shows a light distributor system with an example displacement system in which each elongated rod is captive between a grid-like configuration with flexible joints.

FIG. 12 includes FIG. 12A and FIG. 12B and shows a light distributor system with another example displacement system in which a rod is attached to each elongated rod and can be rotated.

FIG. 13 shows the impact of the displacement of an example light distributor of the "flower" configuration;

FIG. 14 includes FIG. 14A and FIG. 14B and shows another example displacement system in which

FIG. 15 includes FIG. 15A and FIG. 15B and shows the impact of the displacement of the grids of FIG. 14A.

FIG. 16 shows a daily tracking from morning to noon to evening using the displacement of both grids of FIG. 14A throughout the day;

FIG. 17 shows example rotational means used to rotate the light distributor using a rod or cable attached to the light distributor and controlled by an actuator which pulls or pushes on the mobile point on the light distributor, FIG. 17 includes FIG. 17A, FIG. 17B, FIG. 17C and FIG. 17D in which FIG. 17A shows a side view of the light distributor with the rotational means and FIG. 17B, FIG. 17C and FIG. 17D show the rotation of the concentrator supporting section;

FIG. 18 shows another example rotational means used to rotate the light distributor using a gear and translatable rack arrangement, FIG. 18 includes FIG. 18A, FIG. 18B, FIG. 18C and FIG. 18D in which FIG. 18A shows a side view of the light distributor with the rotational means and FIG. 18B, FIG. 18C and FIG. 18D show the rotation of the concentrator supporting section;

FIG. 19 shows another example rotational means used to rotate the light distributor using a pulley and cable arrangement, FIG. 19 includes FIG. 19A, FIG. 19B, FIG. 19C and FIG. 19D in which FIG. 19A shows a side view of the light distributor with the rotational means and FIG. 19B, FIG. 19C and FIG. 19D show the rotation of the concentrator supporting section; and FIG. 20 shows the penetration of light for a "trumpet" light distributor, FIG. 20 includes FIG. 20A and FIG. 20B in which FIG. 20A is the penetration of light without light distributors and FIG. 20B is the penetration of light with light distributors.

It will be noted that throughout the appended drawings, like features are identified by like reference numerals.

DETAILED DESCRIPTION

In order to improve light distribution in an open-ended photo-bioreactor which has an aqueous liquid for a photosynthetic culture, a sun-tracking light distributor can be provided. The light distributor is used to capture light from the sun and distribute it within the volume of aqueous liquid. This light distributor forces some light to travel from above the horizontal surface of the aqueous liquid to a depth within the volume of aqueous liquid.

The photosynthetic culture may comprise algae and other species that use photosynthesis, such as microorganisms. Photosynthetic culture is known to require a light intensity much lower than the maximum solar light intensity. Studies have shown that optimal intensities for photosynthesis can be of the order of 10% of the maximum solar light intensity. Light distribution within an aqueous system is often referred to as "light dilution" in the field of algae culture. The higher the light dilution factor, the more significant the impact on the production of algae.

Figure 1:
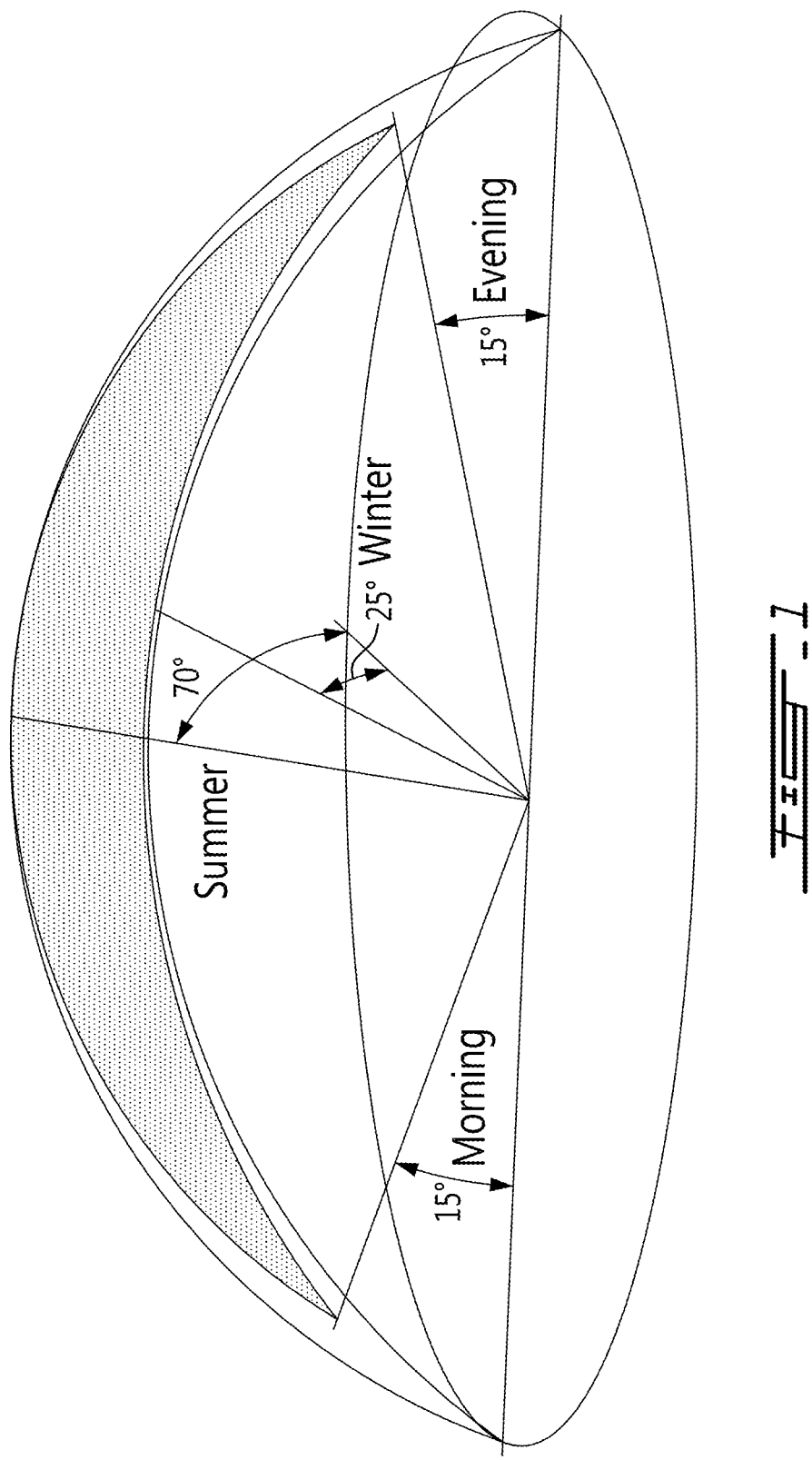
FIG. 1 shows the position of the sun in the sky within daytime and throughout the seasons of the year for locations close to the 45$^{th}$ parallel of latitude.

It is well known that the sun moves westward in the sky during daytime and that its highest altitude (culmination) changes throughout the year, passing from about 68.5° at summer solstice to about 21.5° at winter solstice for locations close to the $45^{th}$ parallel of latitude. At these latitudes the maximum solar altitude at both spring and fall equinoxes is about 45°. FIG. 1 illustrates schematically the sun path for a location close to the $45^{th}$ parallel of latitude.

The light distributor is to be oriented so as to be able to capture a significant portion of the light from the sun and distribute it within the volume of aqueous liquid, regardless of the time of day or day of year.

A sun-tracking light distributor system for an open-ended photo-bioreactor having an aqueous liquid for a photosynthetic culture is therefore provided. The system comprises at least one light distributor and a displacement system adapted to change the orientation of the light entry surface of the light distributor to track the position of the sun using an actuator.

Figure 2:
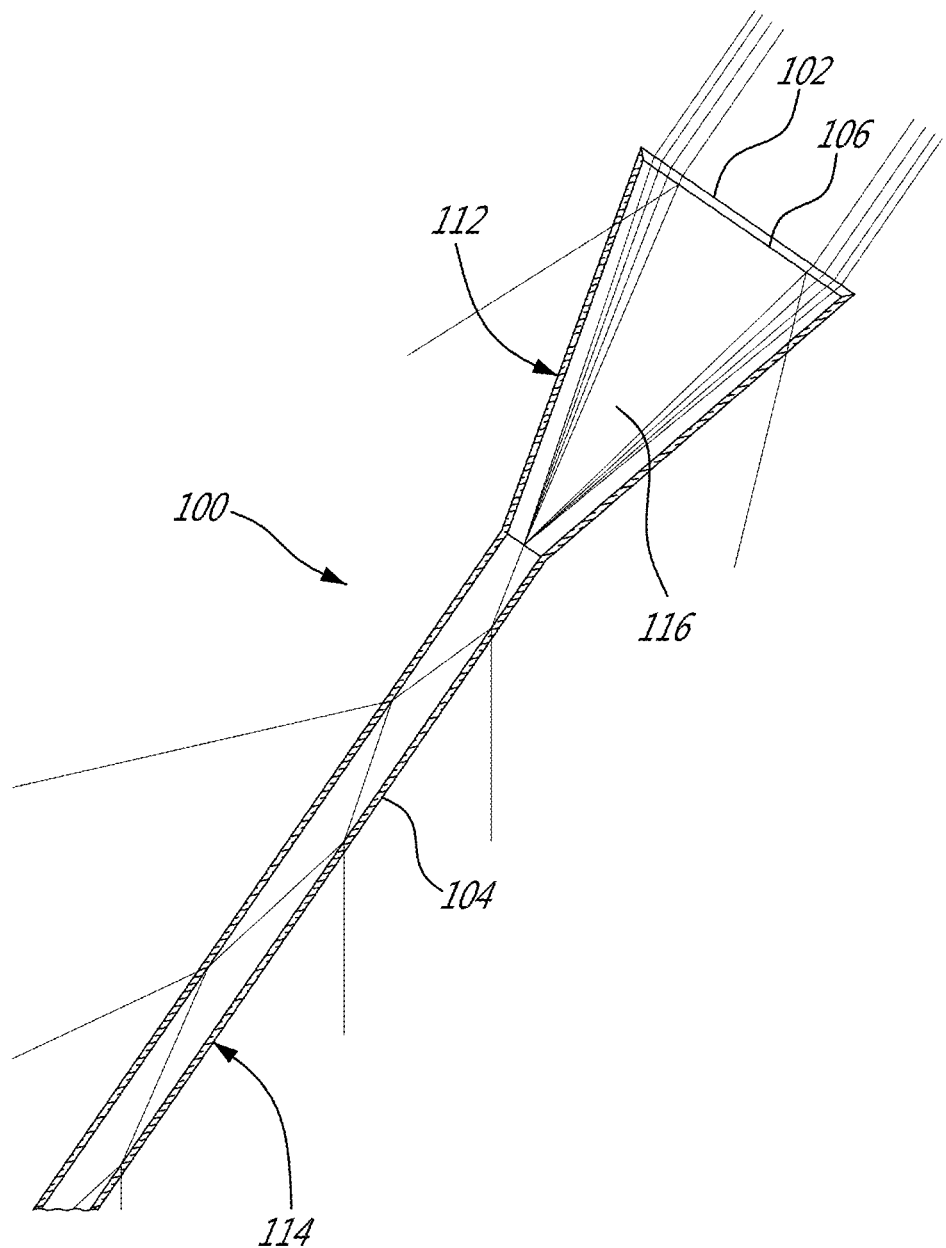
FIG. 2 shows an example light distributor of the "trumpet" configuration.

An example light distributor is shown in FIG. 2. It has a body 100 with a light entry surface 102 which can receive light rays from the sun. In use in an open-ended photo-bioreactor, the light entry surface 102 is provided above the surface of the aqueous liquid.

The body 100 also includes a light distribution surface 104 provided at least partly underneath the surface of the aqueous liquid when in use. The light distribution surface 104 redirects the received light rays within the volume of aqueous liquid.

The body 100 includes a concentrator supporting section 112 and an elongated rod section 114. The light entry surface 102 is at an extremity of the concentrator supporting section 112 and the elongated rod section 114 is at the other extremity. The light distribution surface 104 is defined by the sidewall of the elongated rod section 114. The elongated rod may also be tapered, with the wider end at the concentrator supporting section 112 and the narrower end at the other extremity of the rod. A part of the sidewall may include a reflector arranged to reflect a part of the received light back into the light distributor. Sunlight rays can then be distributed deeper within the aqueous liquid. An example reflector can be a layer of reflective foil applied on a part of the sidewall.

The concentrator supporting section 112 includes a supporting body 116 which allows maintaining a light concentrator element 106 in configuration with the entrance and axis of the elongated rod 114. The light entry surface 102 is at the enlarged end of the concentrator supporting section 112.

The light concentrator element 106 allows propagating light through a channel which has a cross-section smaller than the light entry surface 102. A Fresnel lens is an example of such an optical component 106. Other example light concentrator elements 106 include a standard converging lens of suitable focal length, a mirror (metallic or dielectric) disposed on the side of the concentrator supporting section 112, etc.

Figure 3:
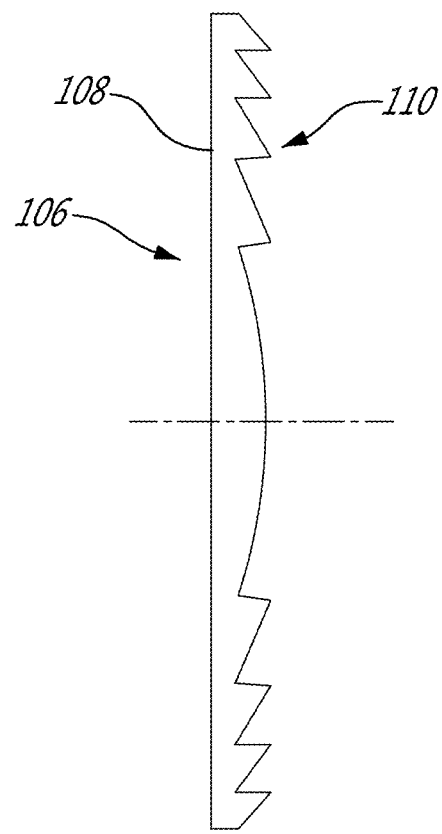
FIG. 3 shows an example Fresnel lens provided at the light entry surface of the example light distributor of FIG. 2.
Figure 4:
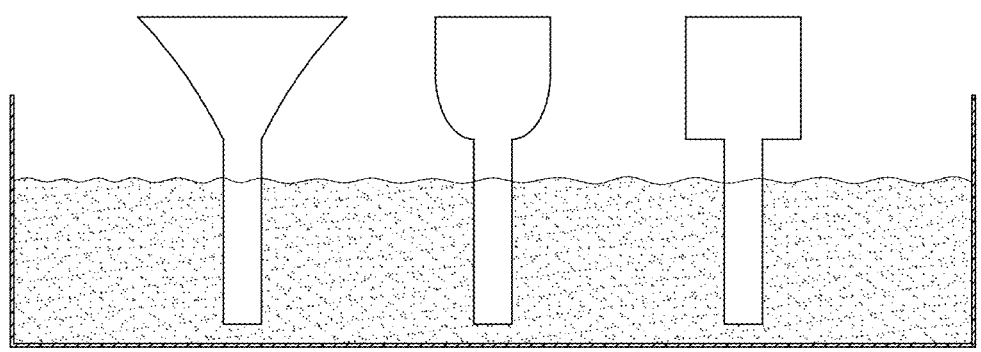
FIG. 4 shows other example shapes for light distributors, the light distributors being provided in an open-ended photo-bioreactor with a volume of aqueous liquid.
Figure 5:
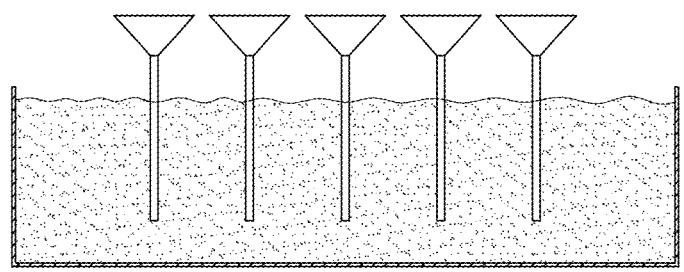
FIG. 5 shows a series of adjacent example light distributors provided in an open-ended photo-bioreactor with a volume of aqueous liquid.
Figure 6:
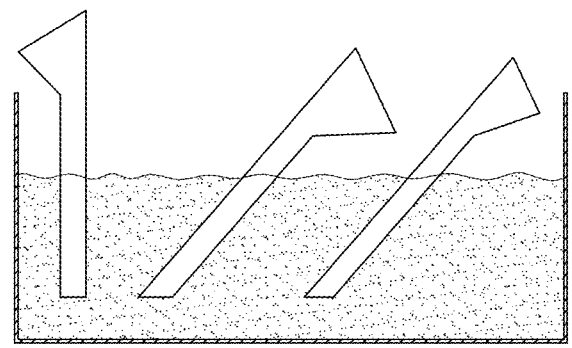
FIG. 6 shows example shapes for light distributors of the "flower" configuration, the light distributors being displaceable within a volume of aqueous liquid.
Figure 7:
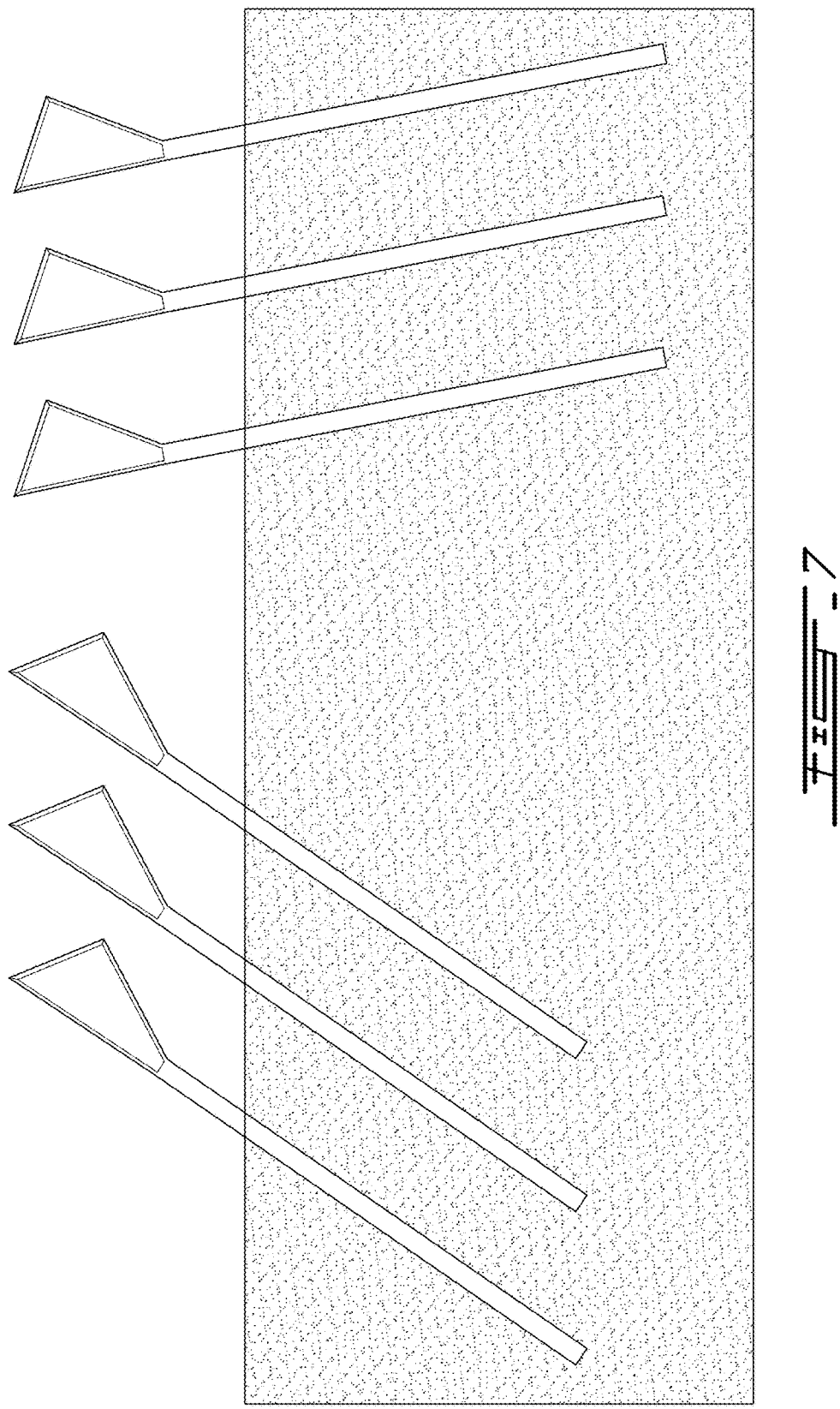
FIG. 7 shows example sun-tracking light distributors being displaceable within the open-ended photo-bioreactor.
Figure 8:
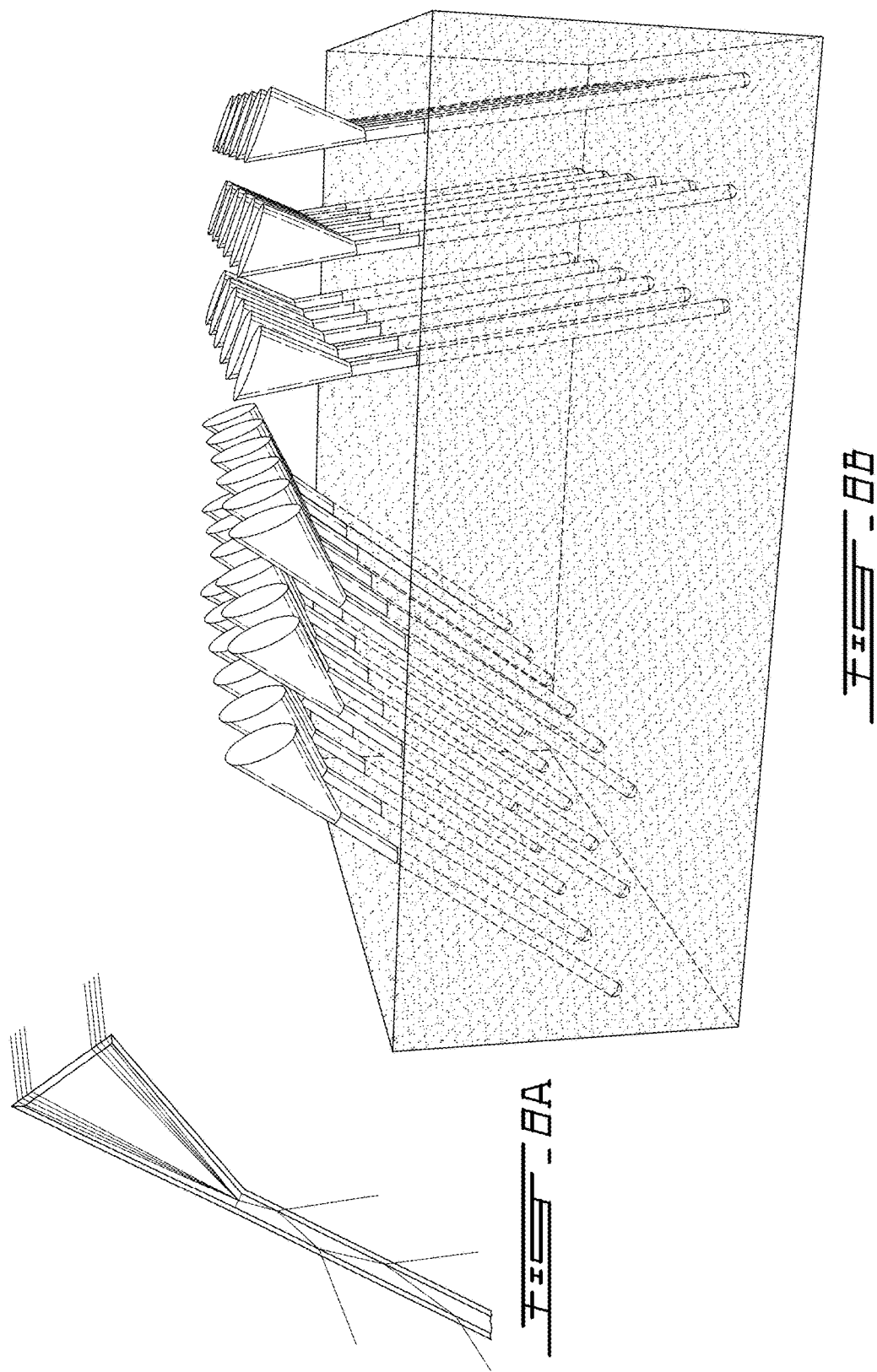
FIG. 8 includes FIG. 8A and FIG. 8B.

An example Fresnel lens 106 is shown in FIG. 3. One of its surfaces is flat 108 while the other is ridged 110. The design of the Fresnel lens allows the fabrication of a lens of large aperture and short focal length, while requiring less material than a conventional lens of similar characteristics. It can therefore be used to redirect the solar rays within the channel. To facilitate cleaning, the flat surface 108 of the Fresnel lens may be set external to the light distributor and the ridged surface may be towards the interior of the light distributor to concentrate the solar rays towards the interior of the light distributor. According to a variant, the flat surface 108 may be towards the interior of the light distributor and the ridged surface 110 towards the exterior of the light distributor.

Other examples of embodiments of the light distributor are found in FIGS. 4 to 9. Various shapes can be used for the concentrator supporting section 112 such as a V-shape, a rounded V-shape, a parabolic shape, a U-shape, a pyramid or conical shape with different possible cross-sectional shapes, etc. Circular, oval or square light entry surfaces are examples of shapes of the light entry surface 102. Many different overall shapes can therefore be used for the light distributor such as a Y-shape, a rounded Y-shape, etc. Various shapes can be used for the elongated rod 114 such as a cylinder, a rectangular prism, a pyramid, etc. The light distributor can be regularly shaped, irregularly shaped or asymmetrically shaped.

As will be readily understood, at some latitudes and for some algae concentrations in the aqueous liquid, it may be preferable to have narrower shapes for the concentrator supporting section, for which the width of the light entry surface is reduced and the length of the light distribution surface 104 is increased.

The concentrator supporting section can be provided at an angle to the rod, see FIGS. 6 to 9. The light distributor can therefore be referred to as being in the shape of a trumpet or Y-shaped (see FIG. 2, FIG. 4, FIG. 5 and FIG. 11) or in the shape of a flower (see FIGS. 7 to 9) with different possible cross-sectional shapes. The angle between the concentrator supporting section and the elongated rod in a flower shaped light distributor will be chosen depending on the particular position of the sun for the region of use. An angle of about 30°, for example, allows to track the sun when it is at zenith and close to the horizon.

Figure 9:
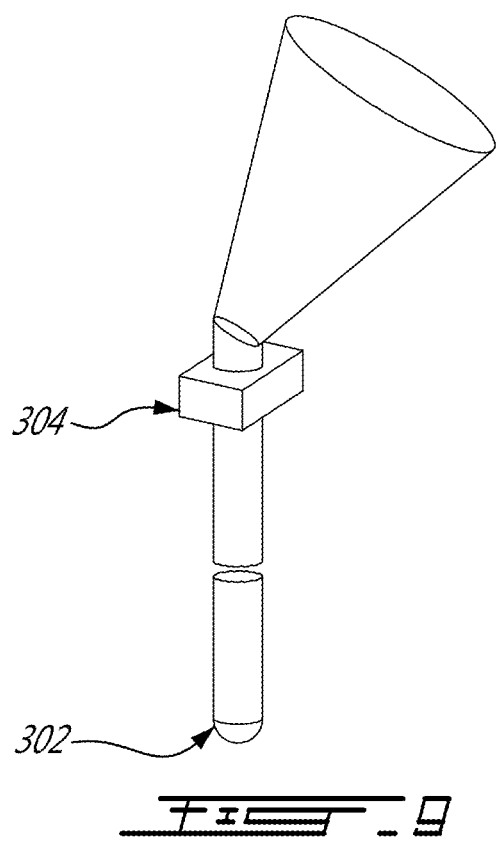
FIG. 9 shows another example light distributor of the "flower" configuration which is weighted by an end cap and is provided with a collar.

The elongated rod may be closed at its bottom to avoid contamination within the rod by the aqueous liquid if the rod is hollow. For example, as shown in FIG. 9, an end cap 302 can be used. The light distributor can be hermetically sealed.

The light entry surface can be covered with a transparent film which can be affixed permanently or temporarily, for example by adhesion to the top of the exterior walls of the body. This transparent film can prevent algae, dirt and aqueous liquid from entering the concentrator supporting section 112 if it is hollow. This transparent film should still allow the light concentrator element to perform its function. This transparent film can be replaced periodically.

A removable transparent film can be applied on the exterior surfaces of the body of the light distributor. This removable transparent film can be removed when it is considered to be dirty. A replacement film is then simply applied on the exterior surfaces. This transparent film can also help in keeping the wall intact and may prevent scratches from being formed in the wall.

The surface area of the light distribution surface may largely exceed that of the light entry surface. For example, the light distribution surface may be 3 times the size of the light entry surface. More particularly, it may be 5 to 10 times the size of the light entry surface.

The light distribution surface allows penetration of light within the volume of aqueous liquid at a depth greater than the natural depth of light penetration in the volume of aqueous liquid. For example, the depth of penetration of light in the volume where light distributors are used can be 3 or even 5 to 10 times the natural depth of light penetration in the same aqueous liquid.

The supporting body 116 and the elongated rod 114 can each be made of plastic, glass or any other transparent material. They are, for example, made of PMMA or polycarbonate. They can be made of extruded plastic material. They are adapted to sustain the pressure from the aqueous liquid. They may be hollow or filled with the material, depending on the characteristics of the light concentrator. A part of the light distributor may be hollow while the other can be filled with material. A liquid or solid material can be inserted therein to facilitate light propagation. For example, dry air, ethanol, glycerol or water may be provided in at least part of the light distributor.

Another example light distributor still has a shape similar to that shown in FIG. 2 with a concentrator supporting section ending in an elongated rod section. However, the light entry surface is now square instead of being round. The light entry surface has a side length of 10 cm, thus creating a 100 $cm^2$ light entry surface. The concentrator supporting section and the elongated rod section are hollow and made of transparent plastic. A Fresnel lens is positioned on the light entry surface. The focal length of the Fresnel lens can be 15 cm. The elongated rod or tube has a diameter of 2 cm, which creates a light distribution surface having a circumference of about 6 cm. A length of 50 cm for the rod allows tripling the surface of the light entry surface. The example light distributor can be placed in an open-ended photo-bioreactor.

As will be readily understood, the walls of the body may be curved along the longitudinal axis of the elongated rod or may bear adjacent longitudinal sections with different angles with respect to the longitudinal axis. Chambers or cavities can be formed in the body.

Figure 10:
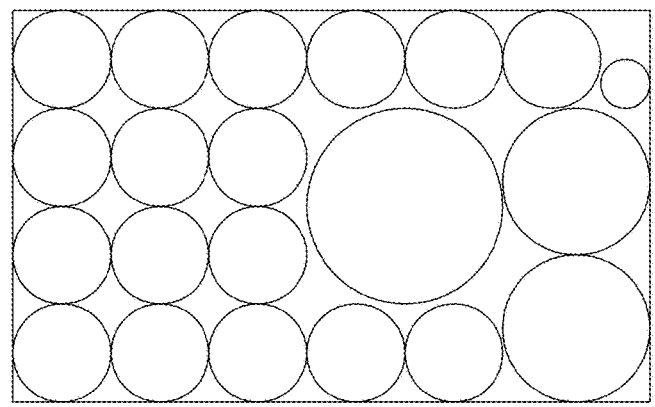
FIG. 10 is a top view of an open-ended photo-bioreactor provided with differently shaped light entry surfaces of light distributors provided in the volume of aqueous liquid.

Multiple light distributors which may or may not be identically sized, are provided in the photo-bioreactor such that the light entry surfaces of adjacent light distributors cover most of the open-ended surface of the photo-bioreactor. See FIG. 5, FIG. 8 and the top view shown in FIG. 10. It is possible to have about 25 example light distributors per square meter, the light distributors being spaced by 20 cm center-to-center.

As shown in FIG. 9, each light distributor can be weighted, for example by an end cap 302 disposed along the length or at the bottom of its elongated rod to stabilize its position in the photo-bioreactor. The elongated rod may be manufactured to include a water chamber to, for example, assist in sinking of the light distributor.

A collar 304 can be added between the concentrator supporting section and the elongated rod section or along the elongated rod section to further help control the position of the light distributor with respect to the photo-bioreactor and/or to give buoyancy to the light distributor. The shape of the collar will be determined as a function of the shape of the rod and/or the concentrator supporting section and the displacement system.

A displacement system allows changing the orientation of the light entry surface of the multiple light distributors in the photo-bioreactor to allow tracking of the position of the sun. The displacement system allows proper positioning of the light entry surface of each light distributor generally towards the sun, depending on its current position in the sky. This displacement system can be individual for each light distributor or can be a global displacement system which controls a plurality of light distributors or all of them.

The displacement system can displace the light distributors along one or two axes. The angle of the elongated rod with respect to the vertical is to be varied along at least one and, in most cases, two directions to tilt the light entry surface towards the sun. In the case of the light distributor in which the concentrator supporting section is at an angle to the elongated rod, namely the "flower" configuration shown in FIG. 7, it may be appropriate to rotate the flower light distributor about itself to change the angle of the light entry surface with respect to the sun.

Figure 11A:
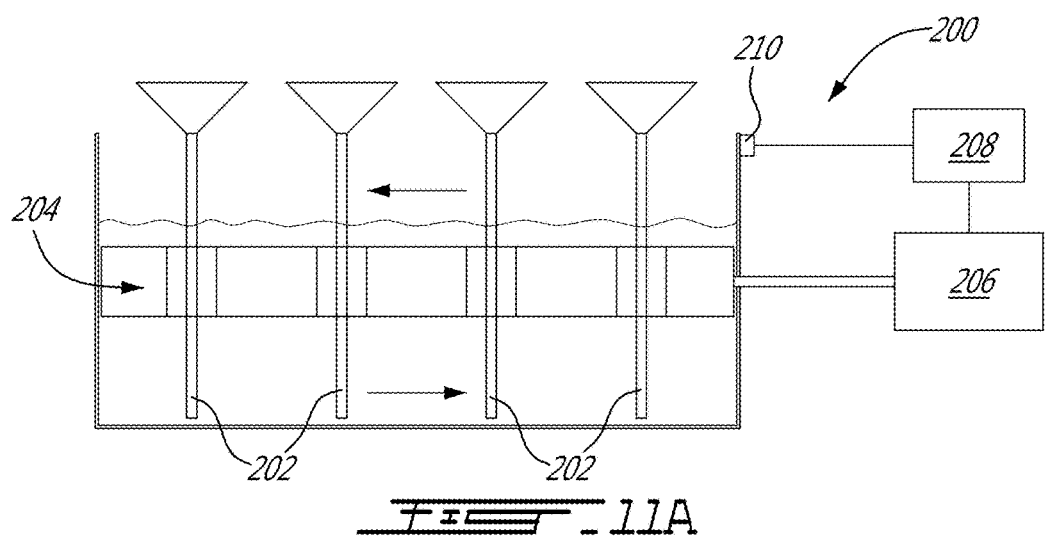
FIG. 11A shows the system prior to an actuation and FIG. 11B shows the system after the actuation of the displacement has occurred.
Figure 11B:
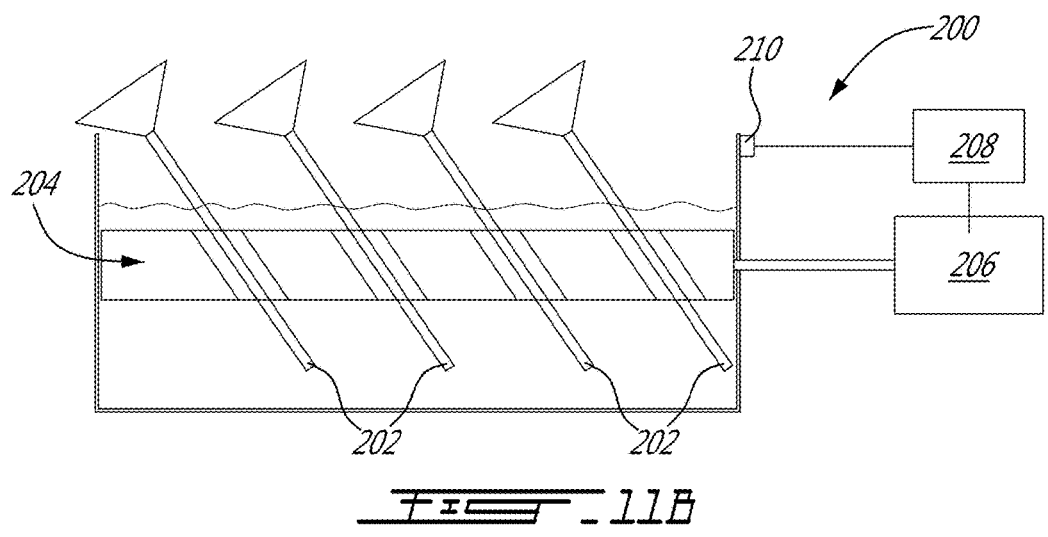

An example displacement system is shown in FIG. 11A and FIG. 11B. In this example displacement system 200, each elongated rod 202 is captive between a grid-like configuration 204 of rods or bars with flexible joints. The grid-like arrangement 204 can be translated and is controlled by an actuator 206. This allows the angle of the elongated rod to be changed in one direction only. The bottom and/or the top of the grid is moved laterally using additional mechanical drive means (not shown) driven by an actuator. FIG. 11A shows the system prior to an actuation and FIG. 11B shows the system after the actuation of the displacement has occurred.

A controller 208 can also be provided to output an actuation command for the actuator(s). A sensor 210 to determine the solar position can further be provided and its output can be used by the controller 208 to determine an appropriate actuation command for the actuator(s). The controller 208 may use stored solar position data to prepare the actuation command. For example, tables including the solar position for the time of day and day of year can be used by the controller 208. The controller 208 may receive a manual input from a user to prepare the actuation command. The actuator(s) may also directly receive a manual input from a user to displace the light distributors.

Figure 12A:
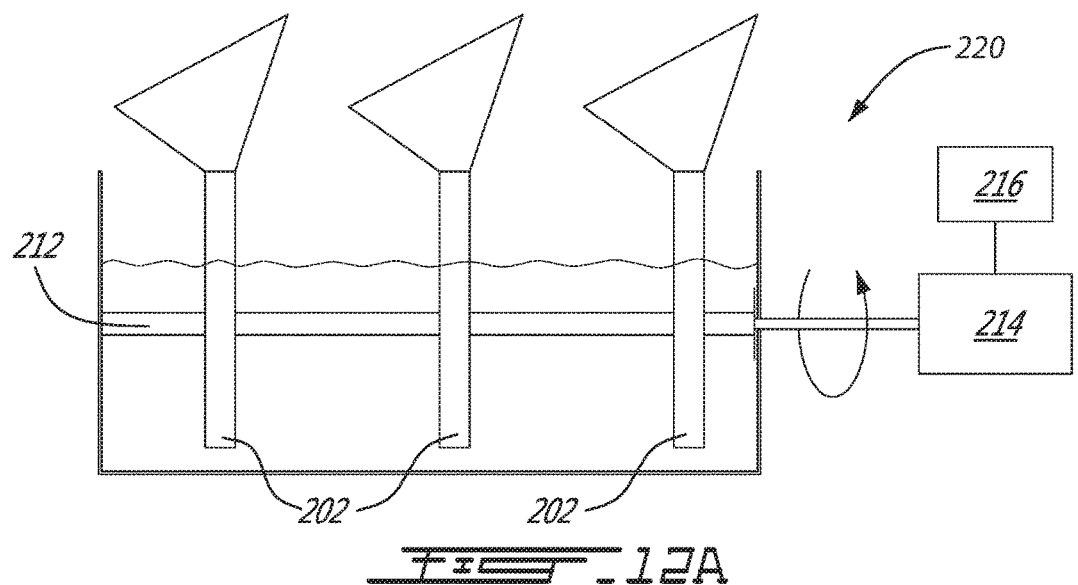
FIG. 12A shows a side view of the system prior to an actuation and FIG. 12B shows an end view of the system after the actuation of the displacement has occurred.
Figure 12B:
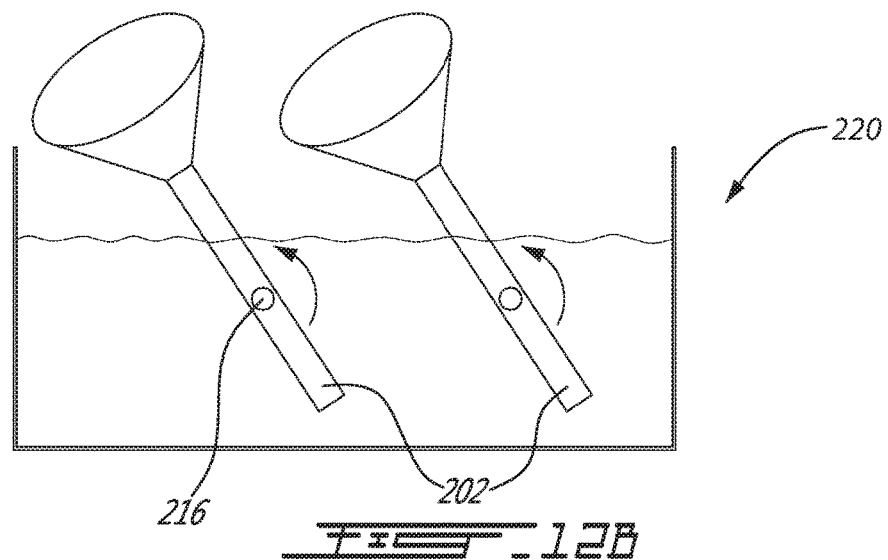

Another example displacement system 220 is shown in FIG. 12A and FIG. 12B. A bar 212 is attached to each elongated rod 202 and can be rotated. It is driven by an actuator 214 receiving a command from a controller 216. This allows the angle of the elongated rod to be changed in one rotational direction only. FIG. 12A shows a side view of the system prior to an actuation and FIG. 12B shows an end view of the system after the actuation of the displacement has occurred.

The impact of the displacement of the flower light distributors is shown schematically in FIG. 13. Depending on the position of the sun, the displacement system controls the orientation of the light entry surface of the light distributors and ensures that the light entry surface is properly oriented to capture a maximal amount of sunlight. The position of the sun in the sky can be followed and tracked throughout the daytime and the year. As will be readily understood, the tracking may be approximate, within a precision range acceptable for the application.

Figure 14A:
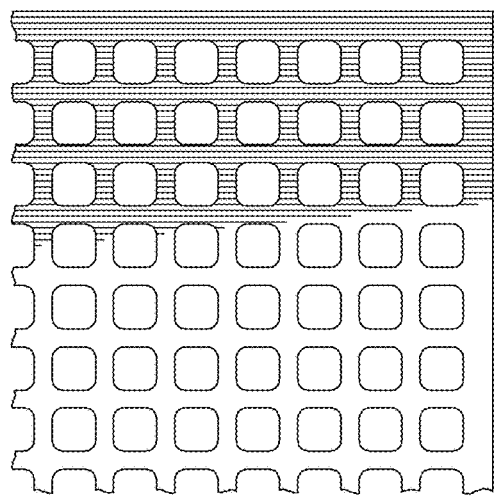
FIG. 14A shows a grid of material and FIG. 14B shows two grids of the type of FIG. 14A being provided at different heights along the light distributors which are provided with a collar.
Figure 14B:
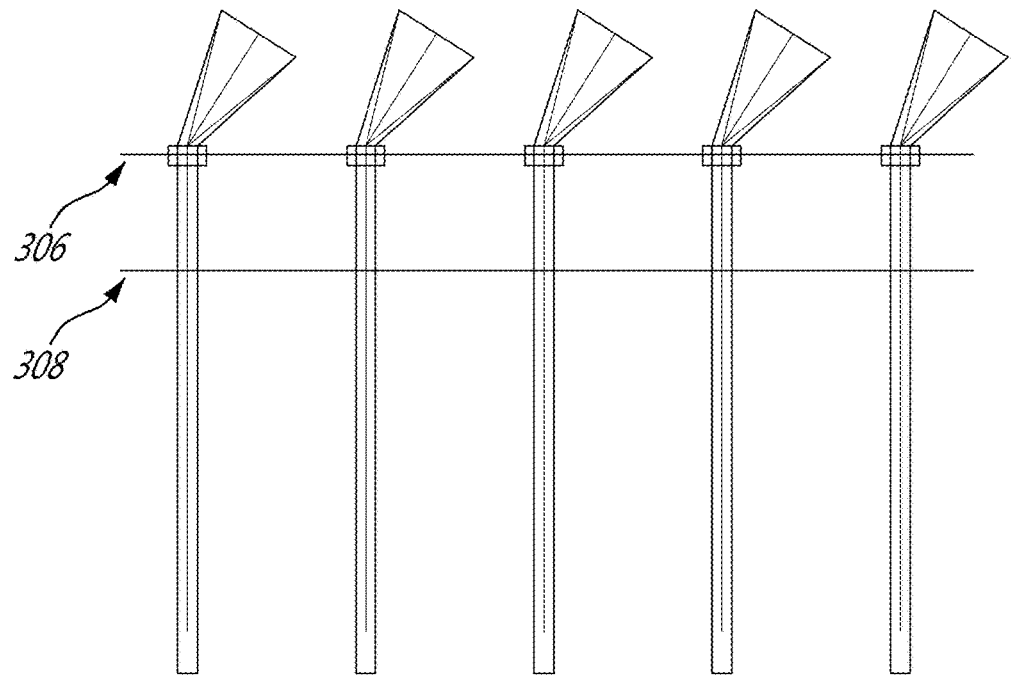

Another example displacement system is shown in FIG. 14. Two grids 306, 308 of material such as the one shown in FIG. 14A are used at two different heights along the length of the light distributor (see FIG. 14B). The grids 306, 308 can be sheets of netted material, metal grids made of bars or rods, perforated platters, wire grids, etc. The first grid 306 can be positioned at the level of the collars and the second grid 308 can be positioned, for example, a few centimeters below the surface of the liquid in the photo-bioreactor. The collars can be adapted to be received and retained within the perforations of the grid 306 while allowing distributor orientation changes. The top grid 306 can allow to control the height of flotation of the light distributors. The grids 306, 308 can also allow to control the distance between the light distributors. As will be readily understood, it is possible to add a second collar along the elongated rod at the location where the second grid is to be placed.

In FIG. 15 and FIG. 16, the impact of the displacement of the grids 306 and 308 is apparent. In a first embodiment, the seasonal tracking of the sun is done by displacing the top grid 306 and the daily tracking of the sun is done by displacing the bottom grid 308 as shown in FIG. 16. In another embodiment, the roles are inverted. In yet another embodiment, the displacement of both grids 306, 308 throughout the day allows to track both the seasonal and daily position of the sun.

Figure 15A:
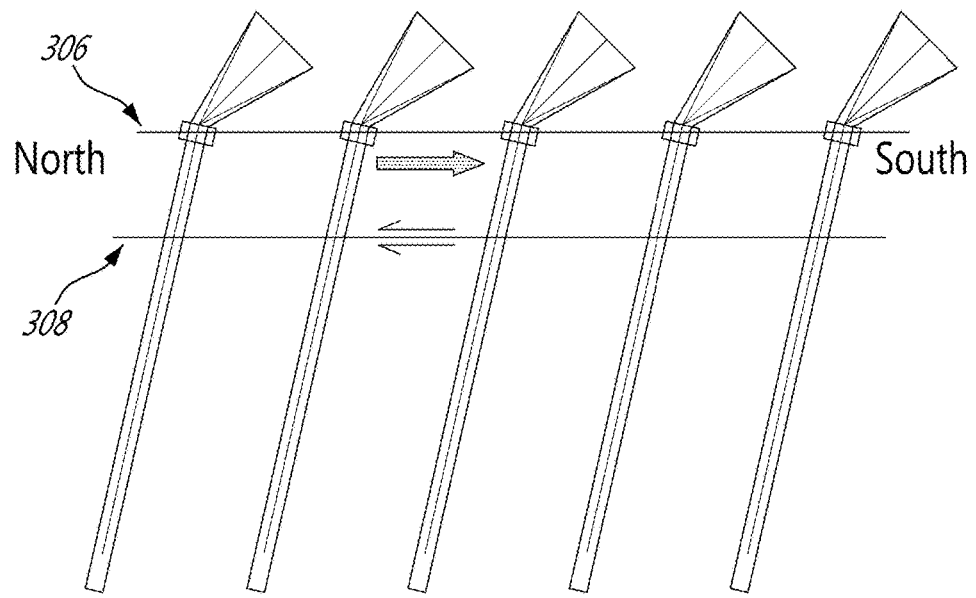
FIG. 15A shows an orientation for the light distributors which would be appropriate for winter and FIG. 15B shows an orientation appropriate for the summer.
Figure 15B:
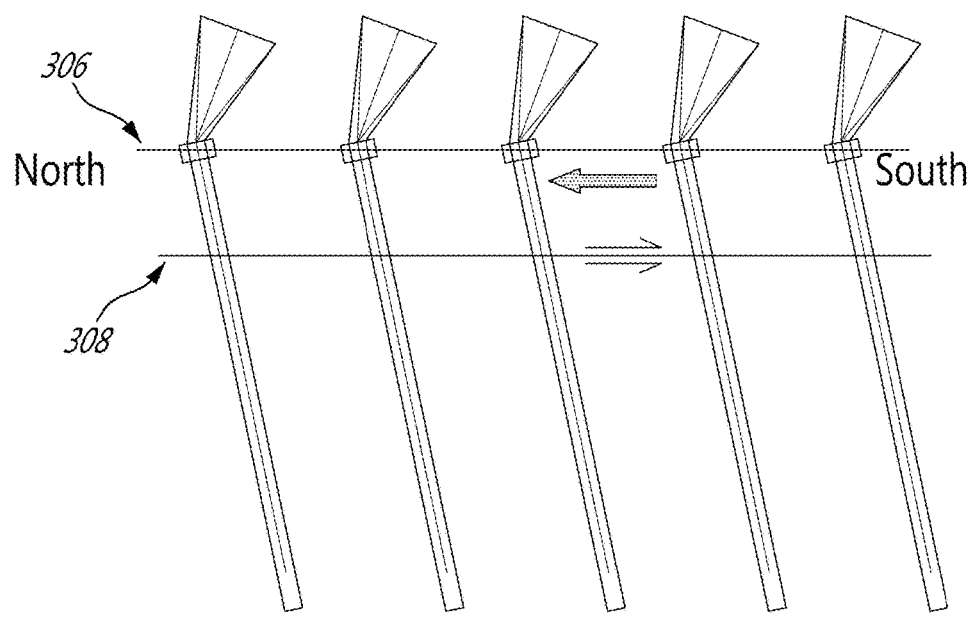

FIG. 15A shows an orientation for the light distributors which would be appropriate for winter and FIG. 15B shows an orientation appropriate for the summer. FIG. 16 shows a daily tracking from morning 310 to noon 312 to evening 314.

In its simplest form, the grid 306 may include a single bar interconnecting aligned light distributors. The bar is adapted to be translated in at least one direction with respect to the photo-bioreactor to change the orientation of the light entry surface of the light distributors. In another embodiment, a second bar can be disposed perpendicularly to the first bar to create a grid 306 interconnecting an array of light distributors. The grid is adapted to be translated in at least one direction with respect to the photo-bioreactor to change the orientation of the light entry surface of each light distributor. In another embodiment, an additional bar or grid is provided at a distance along a longitudinal axis of the elongated rod and the two bars or grids are adapted to be translated independently in at least one direction each with respect to the photo-bioreactor to change the orientation of the light entry surface.

The displacement system which controls a plurality of light distributors may also include a perforated channel for transport and distribution of air, gas and/or $CO_2$ within the aqueous system. A channel for a transparent liquid, for example water with facultative additives can also be provided.

In order to rotate the concentrator supporting section in a flower type light distributor, rotational means can be used. FIG. 17 shows a bar or cable attached to light distributor and controlled by an actuator which pulls or pushes on the mobile point 404 on the light distributor. Alternatively, an articulation can be provided at the fixed point 402 using a second rod or cable to change the fixed point 402 into a second mobile point, thereby allowing the light distributor to rotate upon itself.

FIG. 18 shows a pinion 414 and rack 412 arrangement where each concentrator supporting section is rotated upon translation of the rack 412 with the pinion 414. FIG. 19 shows a pulley 424 and cable 422 arrangement.

Mechanical equivalents which allow to tilt and/or rotate the light distributor so that the light entry surface follows the position of the sun will be known by the person skilled in the art.

The actuators can receive a manual input to change the orientation of the light distributors or can use sensors to detect the position of the sun and orient the light distributors automatically and accordingly. Feedback signals can be used to adjust the position and/or the position can be preprogrammed according to sun position projection data.

It is not necessary to fully track the position of the sun to benefit from light distribution improvement, as long as the light entry surface is generally directed towards the sun. The improvement in light penetration in the photo-bioreactor will be dependent on the actual percentage of light captured and distributed in the volume of aqueous liquid by the light distributors.

As will be understood, it may be determined that the photo-bioreactor algae production is inefficient in winter and is simply paused until spring.

It will also be understood that it may be advantageous to displace the algae to create a flow in the photo-bioreactor, allowing to continuously add water and nutrients after extracting some algae. It has been found that slow macro movements are preferable to rapid micro movements in order to avoid breaking the algae structure. Consequently, the photo-bioreactor may be shaped to allow a periodical displacement of the aqueous liquid with the algae and the light distributors may be installed in a manner facilitating this displacement and allowing the algae to travel, thereby benefiting from the light distribution of each light distributor which may, for any number of reasons, have varying light dilution factors.

As will be readily understood, at the beginning of the production, the algae are in lesser concentration and the light penetration is high. Therefore, light distributors with large light entry surfaces in deep basins may be used. As the production progresses, light distributors with smaller light entry surfaces may be more appropriate and shallower basins may be used. At the end of the production, light distributors with small light entry surfaces are preferable in shallow basins. It may therefore be appropriate to create a basin structure which allows the algae to be transferred from one basin to the next according to its production status and in which the light distributor shape and basin size is adapted to the production status.

Simulations were carried out to determine the difference in light penetration between an open-ended photo bioreactor without solar tracking light distributors and one with solar tracking light distributors. FIG. 20 shows the penetration of light for a Y-shaped light distributor. In FIG. 20A, the results are shown for system without light distributors. In FIG. 20B, the system includes light distributors. As shown in FIG. 20A, most of the sunlight is absorbed in a thin layer at the top of the photo bioreactor and the light intensity in that layer is at least one order of magnitude above the optimal value for efficient algae production. FIG. 20B shows that the light distributors distribute the sunlight in a much larger volume of aqueous liquid and that most of the volume is illuminated with an intensity close to the optimal value.

The embodiments described above are intended to be exemplary only. The scope of the invention is therefore intended to be limited solely by the appended claims.

We claim:

1. A sun-tracking light distributor system for use in an open-ended photo-bioreactor having an aqueous liquid for a photosynthetic culture, comprising:
    at least one light distributor adapted to be at least partly immersed in said aqueous liquid in use, each light distributor comprising a body made of a transparent material allowing sunlight rays to pass therethrough, each light distributor including
        a concentrator supporting section with a light entry surface adapted to receive sunlight rays from above a surface of said aqueous liquid, said light entry surface being at an enlarged end of said concentrator supporting section;
        an elongated rod section with a light distribution surface adapted to redirect the received sunlight rays within said aqueous liquid, said light distribution surface being along a sidewall of said elongated rod section, said light distribution surface being adapted to be at least partly immersed in said aqueous liquid in use, said elongated rod section having an entrance end through which a longitudinal axis of said elongated rod section extends and being in optical communication with said concentrator supporting section to allow the received sunlight rays to travel within the body from the light entry surface to the light distribution surface, said concentrator supporting section being provided at an angle to said elongated rod section;
        a light concentrating element provided at said light entry surface which concentrates within said elongated rod at least a portion of said sunlight rays received at said light entry surface; and
    a displacement system operatively connected to said at least one light distributor and adapted for rotating said concentrator supporting section about the longitudinal axis of said elongated rod section to change an orientation of the light entry surface of said at least one light distributor to track a solar position with respect to at least one axis.

2. The sun-tracking light distributor system of claim 1, wherein said light concentrating element is a Fresnel lens.

3. The sun-tracking light distributor system of claim 1 wherein said concentrator supporting section is cone-shaped with a circular light entry surface and said elongated rod is cylinder-shaped.

4. The sun-tracking light distributor system of claim 1 wherein said concentrator supporting section is shaped as a square pyramid with a square light entry surface and said elongated rod is shaped as a rectangular prism.

5. The sun-tracking light distributor system of claim 1 wherein at least one of said elongated rod section and said concentrator supporting section is made of transparent plastic.

6. The sun-tracking light distributor system of claim 1 wherein at least one of said elongated rod section and said concentrator supporting section is hollow.

7. The sun-tracking light distributor system of claim 1 wherein at least part of an exterior wall of said elongated rod section is provided with a transparent film.

8. The sun-tracking light distributor system of claim 1 wherein said displacement system includes an actuator to change said orientation.

9. The sun-tracking light distributor system of claim 8 wherein said at least one light distributor is a plurality of light distributors and wherein said actuator simultaneously changes said orientation of the light entry surfaces of said plurality of light distributors.

10. The sun-tracking light distributor system of claim 8 wherein said displacement system further includes a sensor for determining said solar position and said controller being configured for controlling said actuator using said solar position obtained from said sensor.

11. The sun-tracking light distributor system of claim 1, wherein said displacement system includes a first bar interconnecting said at least one light distributor, said first bar being adapted to be translated in at least one direction with respect to the photo-bioreactor to change said orientation of the light entry surface of said at least one light distributor.

12. The sun-tracking light distributor system of claim 11, wherein said displacement system further includes an additional bar provided at a distance along a longitudinal axis of said elongated rod section, said first bar and said additional bar being adapted to be translated independently in at least one direction with respect to the photo-bioreactor to change said orientation of the light entry surface of the light distributor.

13. The sun-tracking light distributor system of claim 1, wherein said displacement system further includes a first grid operatively coupled to an actuator, said first grid interconnecting said at least one light distributor, said first grid being adapted to be translated upon control of said actuator in at least one direction with respect to the photo-bioreactor to change said orientation of the light entry surface of said at least one light distributor.

14. The sun-tracking light distributor system of claim 13, wherein said displacement system further includes a second grid provided at a distance along a longitudinal axis of said elongated rod section, said first grid and said second grid being adapted to be translated independently in at least one direction with respect to the photo-bioreactor to change said orientation of the light entry surface of the light distributor.

* * * * *

UNITED STATES PATENT AND TRADEMARK OFFICE
CERTIFICATE OF CORRECTION

Page 1 of 1

PATENT NO. : 9,845,929 B2
APPLICATION NO. : 13/778521
DATED : December 19, 2017
INVENTOR(S) : Marc Levesque, Denis Hotte and Denis Lepine It is certified that error appears in the above-identified patent and that said Letters Patent is hereby corrected as shown below:

In the Claims

Column 10, Line 60, cancel the text beginning with "10. The sun-tracking light distributor system" and ending with "from said sensor." in Column 10, Line 64, and insert the following claim:

--10. The sun-tracking light distributor system of claim 8 wherein said displacement system further includes a sensor for determining said solar position.--

Signed and Sealed this
First Day of May, 2018

Andrei Iancu
*Director of the United States Patent and Trademark Office*